United States Patent
Engel

(10) Patent No.: US 9,001,124 B2
(45) Date of Patent: Apr. 7, 2015

(54) EFFICIENT DETERMINATION OF LIGHTING EFFECTS IN VOLUME RENDERING

(75) Inventor: Klaus Engel, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 617 days.

(21) Appl. No.: 12/881,777

(22) Filed: Sep. 14, 2010

(65) Prior Publication Data

US 2011/0069069 A1 Mar. 24, 2011

(30) Foreign Application Priority Data

Sep. 21, 2009 (DE) .......................... 10 2009 042 328

(51) Int. Cl.
| | |
|---|---|
| G06T 15/50 | (2011.01) |
| G06T 15/08 | (2011.01) |
| G06T 15/60 | (2006.01) |
| A61B 6/00 | (2006.01) |
| A61B 8/00 | (2006.01) |

(52) U.S. Cl.
CPC ................ G06T 15/08 (2013.01); G06T 15/60 (2013.01); *A61B 6/00* (2013.01); *A61B 8/00* (2013.01)

(58) Field of Classification Search
None
See application file for complete search history.

(56) References Cited

U.S. PATENT DOCUMENTS

| | | | |
|---|---|---|---|
| 5,442,733 | A | 8/1995 | Kaufman et al. |
| 2002/0018063 | A1 | 2/2002 | Donovan et al. |
| 2007/0013696 | A1 | 1/2007 | Desgranges et al. |
| 2009/0102843 | A1* | 4/2009 | Sloan et al. ................. 345/426 |
| 2009/0153557 | A1* | 6/2009 | Dimitrov et al. ............ 345/426 |
| 2009/0309877 | A1* | 12/2009 | Snyder et al. ............... 345/426 |
| 2010/0141652 | A1* | 6/2010 | Nutter et al. ................ 345/426 |

FOREIGN PATENT DOCUMENTS

| | | |
|---|---|---|
| CN | 101248459 A | 8/2008 |
| TW | 200931341 A | 7/2009 |
| WO | WO2007023459 A3 | 5/2007 |
| WO | 2009051916 A1 | 4/2009 |

OTHER PUBLICATIONS

Malmer, Mattias, et al. "Fast precomputed ambient occlusion for proximity shadows." Journal of Graphics, GPU, and Game Tools 12.2 (2007): 59-71.*

(Continued)

*Primary Examiner* — Daniel Hajnik
(74) *Attorney, Agent, or Firm* — Lempia Summerfield Katz LLC

(57) ABSTRACT

A two-dimensional representation of an object using volume rendering, with a representation of the object being used in which values of a quantity characterizing the object are given at spatial points of the object, is provided. A blended color value for the representation as pixels on a screen is calculated using a volume rendering technique that does not use an illumination model or uses a local illumination model. At least one ray emanating from a surface of the object is simulated for the purpose of calculating the effect of shadows or the effect of ambient occlusion. A value for the effect of shadows or a value for the effect of ambient occlusion is calculated using the at least one ray. The blended color value and the calculated value are combined in order to obtain a blended color value that takes into account the effect of shadows or ambient occlusion.

16 Claims, 7 Drawing Sheets

(56) References Cited

OTHER PUBLICATIONS

Penner, Eric, and Ross Mitchell. "Isosurface ambient occlusion and soft shadows with filterable occlusion maps." Proceedings of the Fifth Eurographics/IEEE VGTC conference on Point-Based Graphics. Eurographics Association, 2008.*
German Office Action dated Feb. 15, 2011 for corresponding German Patent Application No. DE 10 2009 042 328.1-53 with English translation.
R. Yager et al., "Discrete Ray Tracing," IEEE Computer Graphics and Applications, vol. 12, 1992, pp. 19-28.
C. Dachsbacher at al., "Reflective Shadow Maps," Proceedings of the 2005 Symposium on Interactive 3D Graphics and Games, ACM, New York, 2005, pp. 203-208.
German Office Action dated Jan. 20, 2010 for corresponding German Patent Application No. DE 10 2009 042 328.1 with English translation.
Kniss, J. et al., "Interactive Translucent Volume Rendering and Procedural modeling," Proceedings of IEEE Visualization 2002, pp. 109-116.
Stewart, A.J., "Vicinity Shading for Enhanced Perception of Volumetric Data," Proceedings of IEEE Visualization 2002, pp. 355-362.
Hadwiger, M. et al., "Gpu-Accelerated Deep Shadow Maps for Direct Volume Rendering," Graphics Hardware 2006, pp. 49-52.
Timo Ropinski, Jens Kasten, Klaus Hinrichs, "Efficient Shadows for GPU-Based Volume Raycasting," International Conferences in Central Europe on Computer Graphics, Visualization and Computer Vision 2008, ISBN 978-86943-15-2, pp. 17-24; Others, 2008.
Ropinski, T., et al., "Interactive Volume Rendering with Dynamic Ambient Occlusion and Color Bleeding," Computer Graphics Forum, vol. 27, No. 2, 2008, pp. 567-576.
Zhukov, et al., "An Ambient Light Illumination Model," Rendering Techniques 1998, pp. 45-55.
Levoy, M., "Display of Surfaces from Volume Data," IEEE Comp. Graphics & Application, May 1988, pp. 29-37.
Computergrafik, "4.7 Globale Beleuchfungsmodelle," Deutsches Forschungszentrum für Künstliche Intelligenz GmbH, SS 2004, 20 pages, http://www.dfki.uni-ki.de/-dannen/HTW_Vorlesung/KapiteIO4_4.pdf.eHB, 2004.
Tiede, U., "Realistische 3D-Visualisierung multiattributierter und multiparametrischer Volumendaten," Dissertation, Univ. Hamburg, 1999, pp. i-iv, 1-118.
Chinese Office Action dated Dec. 25, 2013 for corresponding Chinese Patent Application No. 201010290366.9 with English translation.
Chinese Office Action dated Jul. 9, 2014 for corresponding Chinese Patent Application No. 201010290366.9 with English translation.
M. Malmer, et al., "Fast Precomputed Ambient Occlusion for Proximity Shadows," Journal of Graphic GPU and Game Tools, 12, 2, pp. 16-22, 2007.
German Office Action dated Apr. 29, 2014 for corresponding German Patent Application No. 10 2009 042 328.1 with English translation.
Wikipedia, "Volume ray casting," Webpage, http://en.wikipedia.org/w/index.php?title=Volume_ray_casting, pp. 1-2, 2009.

* cited by examiner

EFFICIENT DETERMINATION OF LIGHTING EFFECTS IN VOLUME RENDERING

This application claims the benefit of DE 10 2009 042 328.1, filed Sep. 21, 2009.

BACKGROUND

The present embodiments relate to a method and a device for two-dimensional representation of an object using volume rendering.

The present embodiments lie in the field of volume rendering (e.g., representing or visualizing three-dimensional bodies or objects). Modeling, reconstructing or visualizing three-dimensional objects is used in a wide range of applications in the fields of medicine (e.g. CT, PET, MR, ultrasound), physics (e.g. electronic structure of large molecules) or geophysics (e.g., composition and position of earth strata). The composition of the object under examination may be examined by irradiation (e.g., using electromagnetic waves or sound waves). The scattered radiation is detected, and properties of the body are calculated from the detected values. The result may be a physical quantity (e.g., density, proportion of tissue constituents, elasticity, velocity) with a value calculated for the body. A virtual grid may be used, and the value of the quantity is calculated at the grid points of this grid. The grid points, or the values of the quantity at these positions, may be voxels. The voxels may exist in the form of "gray values."

Volume rendering is used to generate, from the voxels, a three-dimensional representation of the object or body under examination on a two-dimensional display surface (e.g., a screen). In volume rendering, pixels are generated from the voxels (e.g., by the intermediate act of interpolating object points from the voxels), and the image of the two-dimensional image display is composed from the pixels. In order to visualize three dimensions on a two-dimensional display, alpha compositing may be performed. In alpha compositing, voxels, or volume points formed from voxels, are assigned both colors and transparency values (e.g., values for the opacity). "Opacity" may be the transparency or the concealing power of different layers of the body. An object point may be assigned three colors in the form of a three-tuple that codes the red, green and blue color components ("RGB value"), and an alpha value that parameterizes the opacity. Together, these parameters form a color value RGBA, which is combined or blended with the color values of other object points into a color value for the pixel (for visualizing partially transparent objects, blending may be performed using alpha blending).

In one embodiment, an illumination model is employed for assigning a suitable color value. The illumination model takes into account lighting effects (e.g., reflections of the light at the outer surface or surfaces of inner layers of the object under examination) under modeled or simulated irradiation of the object for visualization purposes.

The literature contains a number of illumination models that are used. A commonly used model, for example, is the Phong or Blinn-Phong model.

Ray casting (i.e., simulating incident light rays to display or visualize the body) may be used for volume rendering.

In ray casting, imaginary rays that emanate from the eye of an imaginary observer are sent through the body under examination or object under examination. Along the rays, RGBA values for sampling points are determined from the voxels, and combined into pixels for a two-dimensional image using alpha compositing or alpha blending. This process may take account of illumination effects using one of the illumination models discussed above as part of a method referred to as "shading."

For applications in which manipulations (e.g., perspective changes, color changes, clippings) involve performing volume rendering again for every change, the illumination model may only take account of local effects because otherwise, unacceptable delays may be experienced by the user during the application. This results in significant reductions in quality, however. A more realistic representation may be achieved by methods that also take into account global effects. In this case, it is useful to differentiate between two effects, because of the different methods used in computation. The first effect is shadows. The result of the shadow effect is that for a point on a simulated ray through an object, the path between the point and the existing light source or light sources contains obstructions (e.g., the light ray cannot reach the point unobstructed). A method for computing this shadow effect is to send a ray from the observed point towards the light source (or to send rays to the different light sources) in order to determine which components of the light may penetrate to the point.

The effect of diffuse light (e.g., "ambient occlusion") is distinguished from the shadow effect. This ambient occlusion effect is caused by diffuse light and is important because the ambient occlusion makes structures visible that are not visible solely by the direct light. The light scatter may result in light hitting an object from all directions. The diffuse light may be absorbed by matter, resulting in non-uniform illumination of the object by the diffuse-light component. An example of this effect is the corners of a room that appear darker than the center of the room. The absorption of diffuse light is examined by the same method, for example, that is also used to calculate the shadows. Since the diffuse light does not come from a fixed source, however, but from all directions, rays are emitted in a stochastic manner from a hemisphere that corresponds locally with a surface, and an assessment thereby performed as to how much diffuse light is absorbed. "Ray tracing" may be sending rays to determine illumination properties, and "Monte Carlo ray tracing" may be stochastic ray sampling using ambient occlusion. Zhukov et al. have presented a definition for ambient occlusion. See Zhukov, S., et al., "An ambient light illumination model," *Rendering Techniques* '98 (1998): pp. 45-55. According to this definition, the value of the ambient occlusion at a point of a surface is the amount of light of the ambient light that may reach this point.

Ray tracing methods are highly complex. Rays are generated from each sampling point on the simulated ray (e.g., one ray for each light source, and a multiplicity for ambient occlusion). Ray-tracing methods may also be "brute-force" methods, again with regard to this complexity. The corresponding complexity may be too high for interactive changes to the representation of the object, which is why a more realistic representation of illumination effects is often dispensed with, even though shadows and ambient occlusion are global effects. Current methods, which take into account global illumination effects, use either extensive data pre-processing and/or the construction of additional, pre-computed data structures (deep shadow maps, see Hadwiger, M., et al., "Gpu accelerated deep shadow maps for direct volume rendering," *Graphics Hardware*, Proceedings of the 21st ACM SIGGRAPH/EUROGRAPHICS Symposium on Graphics Hardware (2006): pp. 49-52; shadow mapping, see Kniss, J. et al., "Interactive Translucent Volume Rendering and Procedural Modelling," *Visualization*, Proceedings of the conference on Visualization '02 (2002): pp. 109-16; summed area tables, see U.S. Provisional Application No. 60/698,830; computing local histogramms, see Ropinski, T., et al., "Interactive volume rendering with dynamic ambient occlusion and color bleeding," *Computer Graphics Forum*, Vol. 27, No. 2 (2008): 567-76; and vicinity shading, see Stewart, A. J., "Vicinity shading for enhanced perception of volumetric data," *Visualization*, Proceedings of the 14th IEEE Visualization 2003 (2003): pp. 355-62). Other methods are limited by their potential applications (e.g., half-angle slicing cannot be applied to ray casting, for example).

SUMMARY AND DESCRIPTION

The present embodiments may obviate one or more of the drawbacks or limitations in the related art. For example, low-complexity representation of lighting effects may be provided.

According to the present embodiments, the representation of an object is based on volume rendering that does not use an illumination model or only a local illumination model (e.g., Blinn-Phong model).

The object exists in the form of voxels (i.e., in the form of scalar values of a quantity characterizing the object (e.g., the density) that are given at spatial points of the object). In other words, a scalar array is given as a function of the position for a plurality of spatial points. "3D representation of the object" is also used below to refer to this representation of the object by voxels.

Volume rendering maps the 3D representation onto two dimensions for display by a screen. This mapping produces pixels or image points for a 2D image. "Voxel" is used below solely for 3D representations and "pixel" is used solely for 2D representations.

The voxels are obtained by a measuring system, for example. Typical examples are measurements by computer tomography, which provide projections for different recording positions, from which the voxels are reconstructed. Other possibilities are ultrasound techniques or magnetic resonance images. The voxels may exist in the form of "gray values," which are a measure for the respective density of the object at the respective position.

Direct volume rendering techniques such as ray casting may be used. Visual rays incident on the object are simulated. Along the visual ray, values of the characterizing quantity are calculated, color values are assigned to the calculated values, and the color values for displaying as pixels on a screen are superimposed to produce a blended color value (RGB: possibly three values). The blended color value is mostly in the form of RGB values or RGBA values. "Color value" may include the various forms of color representation. "Color value" may also include representation in the form of three or four values as RGB values or RGBA values, respectively.

According to the present embodiments, the result of volume rendering is corrected in order to take account of lighting effects (e.g., the effects of shadows and ambient occlusion).

A correction is performed for at least one of the effects of shadows and ambient occlusion. The correction is calculated or determined in a similar manner for both cases. Like for a "brute force" computation, at least one ray is simulated, which as a test ray, detects, section by section, contributions to the lighting effects. The contributions along a ray are accumulated into a cumulative contribution of the ray. The number of rays and the direction of the rays may depend on the investigated effect. To take account of shadows, one test ray may be emitted towards each light source. For ambient occlusion, a plurality of test rays are emitted in different, for example, stochastically selected directions. The calculation of both effects may be made in one act, with, if applicable, one or some of the simulated rays being used for both effects. For a plurality of rays (e.g. a plurality of rays for ambient occlusion), the results for the individual rays may be combined in one result, where the individual rays may be weighted.

Unlike the conventional "brute force" techniques, the correction is not computed for the individual sampling values (e.g., of a ray in ray casting), but may be calculated only once per ray-casting ray or once per blended color value or pixel.

The starting point for the test rays for calculating a correction for shadows and/or ambient occlusion is located on a surface of the object. In one embodiment, the surface of the object is an outer surface. It may also be practical, however, according to the composition of the object, to start from an inner surface (e.g., if the outermost material or tissue layer of the object is practically transparent).

In a ray casting technique, the start point would be, for example, the entry point of a simulated ray-casting ray into the object (e.g., practical for a front-to-back technique) or the exit point from the object (e.g., practical for a back-to-front technique).

A value for the effect of shadows, a value for the effect of ambient occlusion, or values for both the effect of shadows and the effect of ambient occlusion is calculated using at least one test ray.

The blended color value obtained with volume rendering is combined with the calculated value in order to obtain a blended color value that takes into account the effect of shadows, the effect of ambient occlusion or the effect of shadows and ambient occlusion. The blended color value may be a combination of the blended color value with solely or exclusively the calculated value for taking into account the effect of shadows or the effect of ambient occlusion (apart from any effects taken into account by local illumination models in the volume rendering act).

The approximation performs only one calculation of the effects of "shadows" and/or "ambient occlusion" for the blended color value or for a pixel. For many classes of objects, the approximation results in a very slight loss in quality compared with the correct procedure, which performs, for example, the correction for a pixel for sampling values along an entire ray-casting ray. In a certain sense, one has a correction at the pixel level (e.g., in 2D space), instead of correction at the voxel level.

In comparison, the complexity is significantly lower (e.g., more than one order of magnitude), so that re-calculations may be performed on currently standard hardware fast enough for interactive operations on the visualized object (e.g., rotation, editing, changing light sources).

The complexity may be reduced further according to the present embodiments by limiting the length of the test rays or by calculating the effects of shadows and/or ambient occlusion only for some of the pixels and obtaining the missing values by interpolating the calculated values.

DETAILED DESCRIPTION OF THE DRAWINGS

Figure 1:
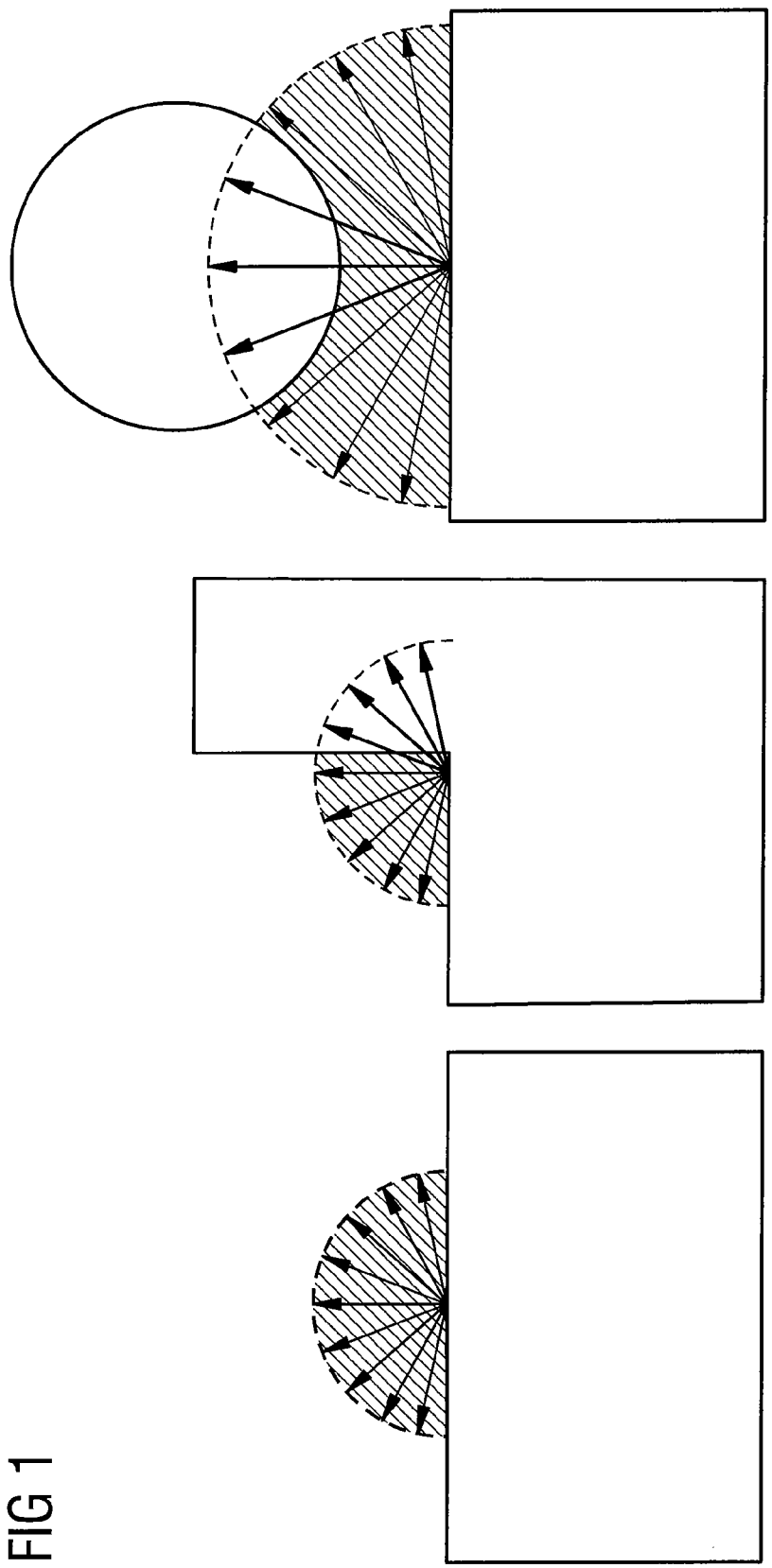
FIG. 1 shows an illustration of ambient occlusion.

Ambient occlusion is a simplified approach to calculate the effect of diffuse light in an ambient area around an object. The diffuse light may come from all directions. As a result of local shadows, less light reaches hollows and corners of the objects, so that the hollows and corners appear darker than smooth areas. A direct (brute force) approach to the approximation of such diffuse-light effects would be to emit a large number of simulated test rays in different directions for each sampling position in the ray casting, in order thereby to detect light-absorbing structures and to take into account the corresponding light absorption. If the sampling position lies on an implicit surface, the rays may be emitted over a hemisphere above the implicit surface. This is shown more closely in FIG. 1. In case a, in FIG. 1, rays are emitted such that the rays are distributed over a hemisphere. The rays do not meet any obstruction, so that no darkening occurs in the context of ambient occlusion. In case b, an absorbing wall exists on the right-hand side, so that approximately 50% occlusion (e.g., darkening) prevails. In case c, a spherical absorption structure exists, so that approximately one third of the rays (in FIG. 1, 3 rays out of 9) are absorbed. In this case, there is approximately 33% occlusion or absorption.

Figure 2:
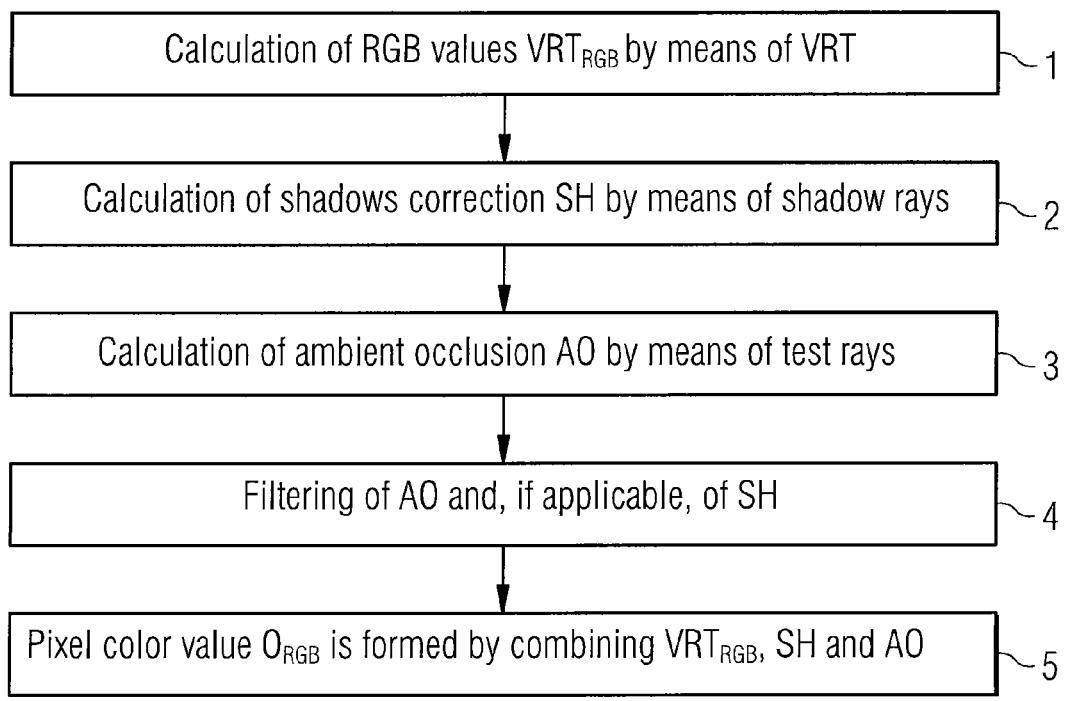
FIG. 2 shows a schematic diagram of one embodiment of a method for two-dimensional representation of an object using volume rendering.

A direct method (brute force) may use a very large amount of computing time and memory, because a large number of sampling points are sampled during a ray casting. This consideration applies to the global computation of shadows (e.g., screening of the light incident directly from the light sources in the simulation). For the shadows, in a "brute force" algorithm, test rays are emitted towards each light source. This procedure involves a very large degree of complexity, which makes interactive manipulations of the visualized object (e.g., changing, editing the object) difficult in real time. One of the present embodiments is now presented in greater detail with reference to FIG. 2. In a first act, a standard ray-casting method is performed (e.g., using a local illumination model or taking no account of illumination effects). This results in blended RGB values being obtained by alpha blending, which essentially include a first approximation for the pixel to be computed. Sampling artifacts may also be suppressed by stochastic jittering.

In a second act, test rays are emitted from a surface of the object towards the light sources in order to calculate the effect of shadows. The result is a value between 0 and 1, which is a measure of the shadow effect (0=completely in shadow, 1=no shadow). The test rays or shadow rays either encounter absorbing structures and produce a cumulative shading effect, or reach the light unobstructed. The result of all shadow rays may be combined into a shadow image formed using gray values.

In a third act, the global absorption of diffuse light is taken into account. Once again, test rays are emitted from a surface of the object (e.g., in a number of randomly selected directions above a hemisphere of the surface; cf. FIG. 1). The effect of the matter or the volume that is encountered along the rays is evaluated and accumulated into a cumulative value. The results may be combined into an image.

Acts 2 and 3 may also be combined; any individual rays may be used both for computing the shadows and computing the diffuse-light absorption.

In a fourth act, the result of the diffuse-light absorption computation is filtered, for example, by a Gaussian filter or a bilateral filter. In one embodiment, the shadow image may also be filtered in this way.

In a fifth act, the results from the first, second and third acts are combined with each other. A combined color value $O_{RGBA}$ (e.g., a resultant GBA value) may, for example, be calculated using the rules a.-d. given below. $O_{RGB}$ may be the RGB component, $O_A$ for the alpha value, volume rendering technique (VRT) or $VRT_{RGBA}$ for the result calculated in the first act using conventional volume rendering. Shading may be taken into account in a local illumination model or even ignored completely (cf. $VRT\_Unshaded_{RGB}$ in rule d.). SH (shading) is the result of the second act for the shadow computation, and AO (ambient occlusion) is the result of the third act for the ambient occlusion. The term "ambient" is a factor that comes from a local illumination model (e.g., Phong model). In the local illumination model, the factor is a component of the reflected light that does not depend on the incident direction of the reflected light. The value of the factor may be expressed as the product of the intensity of the ambient light and a material constant. The following rules may be applied using these notations:

$O_{RGB}=VRT_{RGB}*SH+ambient*AO*VRT_{RGB}$,
$O_A=VRT_A$     a.

$O_{RGB}=VRT_{RGB}*SH+ambient*AO, O_A=VRT_A$     b.

$O_{RGB}=VRT_{RGB}*SH*AO, O_A=VRT_A$     c.

$O_{RGB}=VRT_{RGB}*SH+ ambient*AO*VRT\_Unshaded_{RGB}, O_A=VRT_A$     d.

According to the present embodiments, the resource-intensive shadow and occlusion computation is performed in the screen domain, (i.e., the pixel domain). In other words, only one shadow computation or occlusion computation is performed for each pixel on the screen, respectively, and shadow computations or occlusion computations are no longer made along a ray. This is an approximation, and is theoretically less accurate than "brute force" methods, which compute shadows and ambient occlusion along an entire ray. This approximation, however, produces results that have scarcely been reduced in quality for many objects, as is illustrated below with reference to the figures.

The methods of the present embodiments work well with transfer functions having low transparency. Transfer functions having large semi-transparent parts may result in image artifacts. Opaque transfer functions, however, are very common, for example, in bone visualization in medical applications or for visualizing industrial CT data sets.

Since ambient occlusion and shadows are effects that have a low frequency (i.e., low variation), a different resolution may be used in the method (e.g., shadows (SH) and ambient occlusion (AO) are computed using a lower resolution than the original volume rendering (VRT)). For combining the VRT, SH and AO images, interpolation may be used for the images having lower resolution (e.g., SH and AO images).

Figure 3:
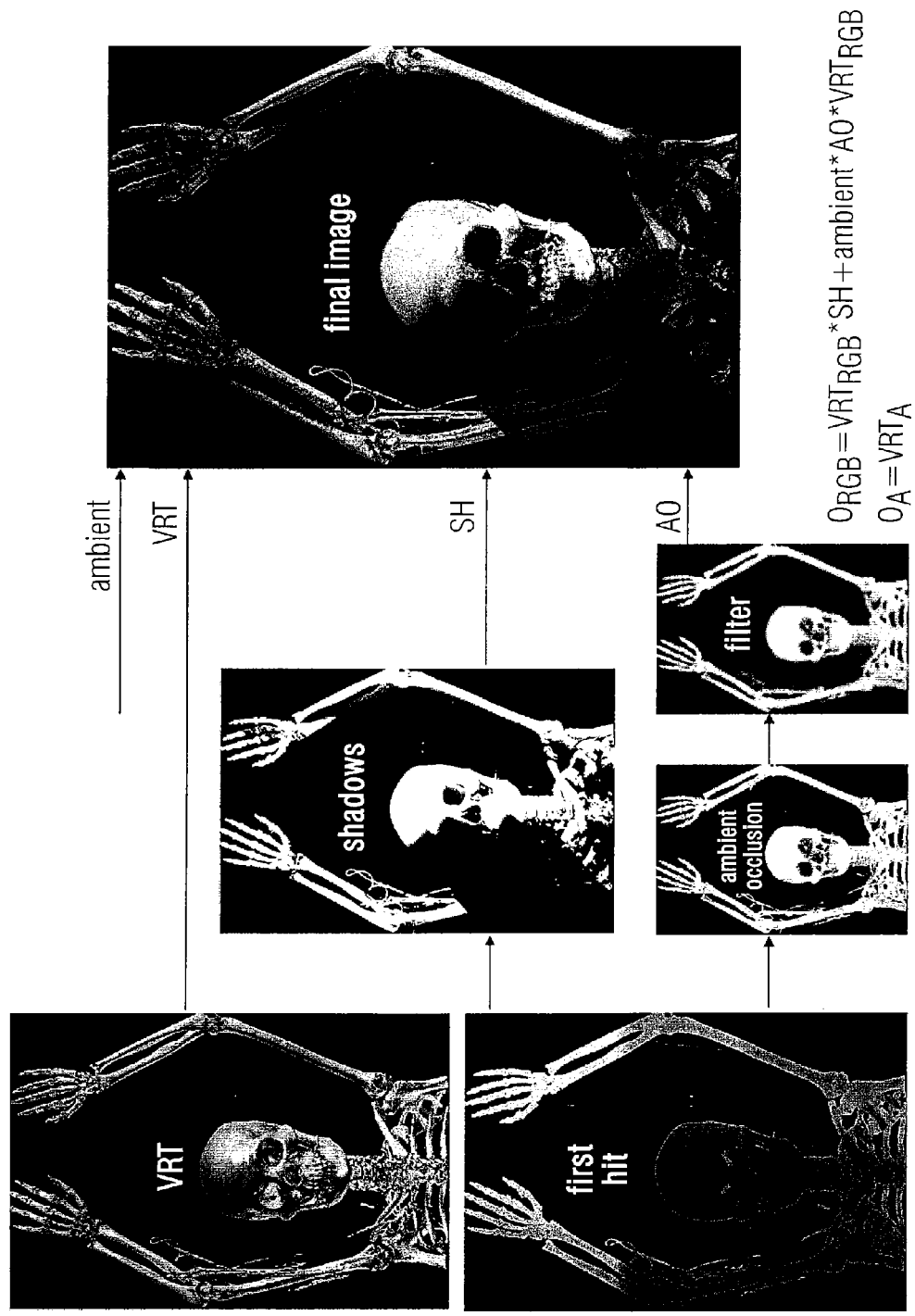
FIG. 3 shows an image composed according to one embodiment of a method for two-dimensional representation of an object using volume rendering.
Figure 4:
FIG. 4 shows a comparison of images to illustrate the image quality of images produced according to one embodiment of a method for two-dimensional representation of an object using volume rendering.

FIG. 3 shows graphically how the method works. In the top-left, an image labeled VRT is shown that has been recorded conventionally without global illumination effects. Underneath, the image referred to as "first hit" is shown (e.g., the image that is obtained from the beams hitting an absorber for the first time). The "first hit" image approximates very closely the complete image (e.g., the image labeled VRT). The "first hit" image provides the start positions for the global computation of the shadows ("shadows" image) and of the ambient occlusion (in the "ambient occlusion" image). The "ambient occlusion" image undergoes additional filtering ("filter" image). All the images are combined using the formula shown in FIG. 3 (formula a. given above). FIG. 4 shows four images. In the top-left, the VRT image recorded using local illumination effects is shown. The shadow image computed according to the present embodiments is shown in the bottom-left. The combined image from the two left-hand images (VRT with AO) is shown in the top-right. The image that would be obtained if the brute force method were to be performed in full to compute the shadows is shown in the bottom-right of FIG. 4. A slight difference resulting from the approximation made for the object under examination may be seen in the comparison of the images in the top-right and bottom-right. The subsequent images are used to clarify this further.

Figure 5:
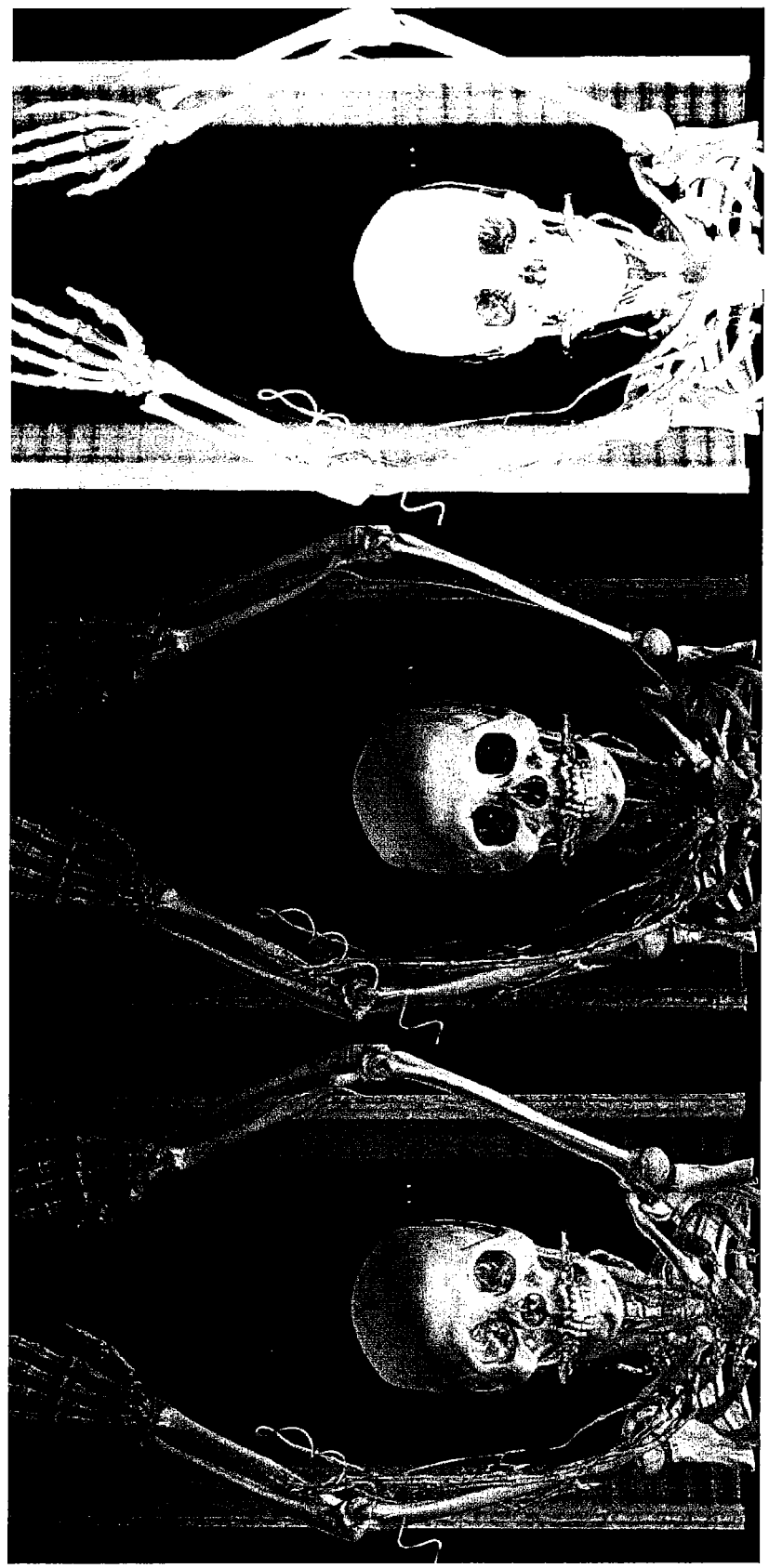
FIG. 5 shows a representation of three elements, from which one image is composed according to one embodiment of a method for two-dimensional representation of an object using volume rendering.

FIG. 5 shows on the left an image that has been calculated using local illumination (VRT image). On the far right is the image from ambient occlusion (AO image) and in the center is the combined image (VRT with AO).

Figure 6:
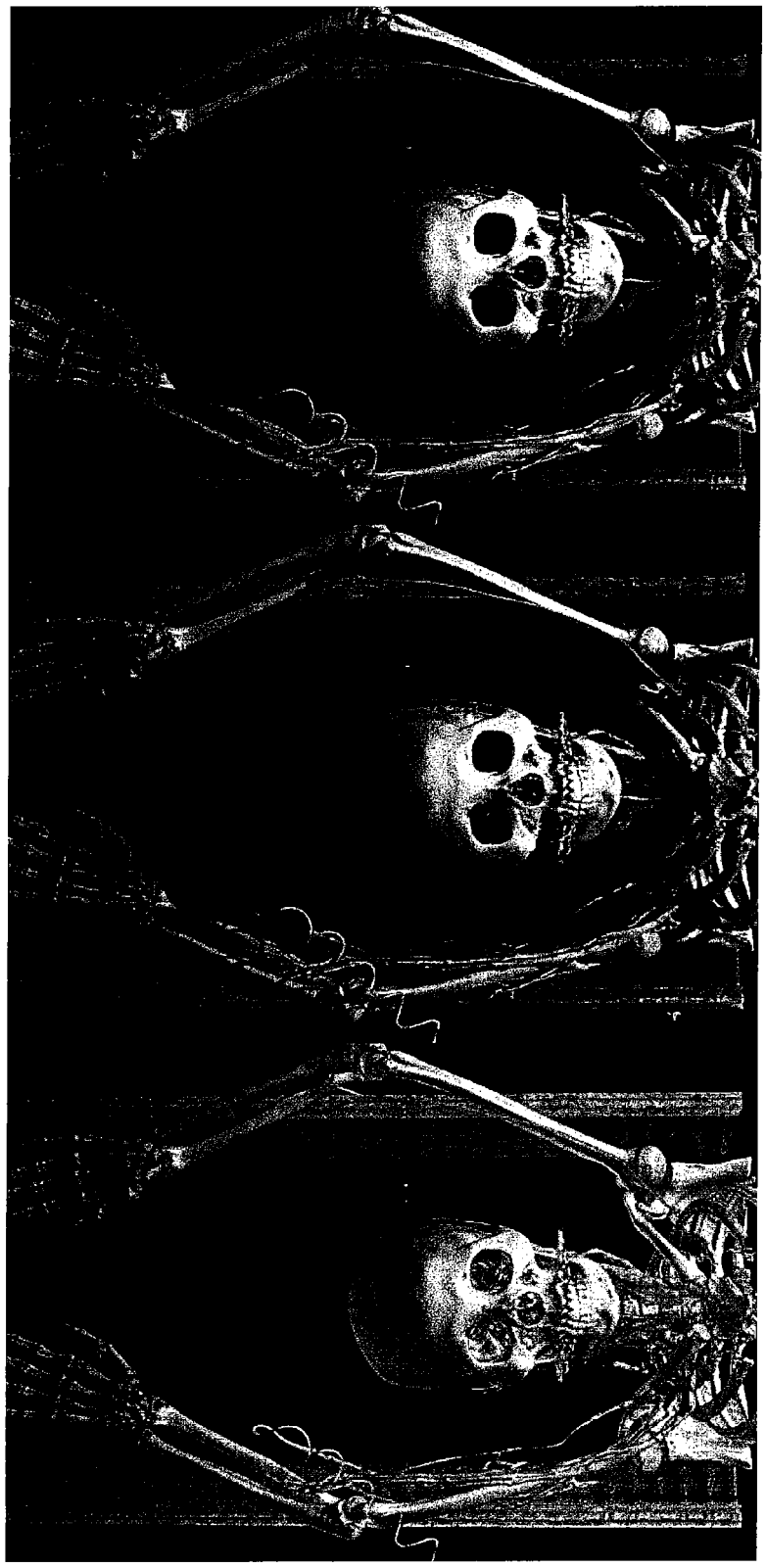
FIG. 6 shows a comparison of image quality for different illumination models.

FIG. 6 shows again on the left the image that includes the local illumination effect (VRT image). In the center is shown the image that would have been obtained according to the present embodiments using shadows and ambient occlusion (VRT with SH and AO), and on the far right is the image in which the "brute force" method is performed without approximation. The comparatively good-quality of this approximation is apparent from the slight differences between the images on the right and in the center.

The present embodiments may be implemented in various forms of hardware, software, firmware, special-purpose processors or a combination thereof. An implementation on a graphics processing unit (GPU) using open graphics language (OpenGL). In one embodiment, the OpenGL Shading Language is used.

The present embodiments may be implemented in software as an application program. The application program may be uploaded and executed on a machine that has any suitable architecture.

Figure 7:
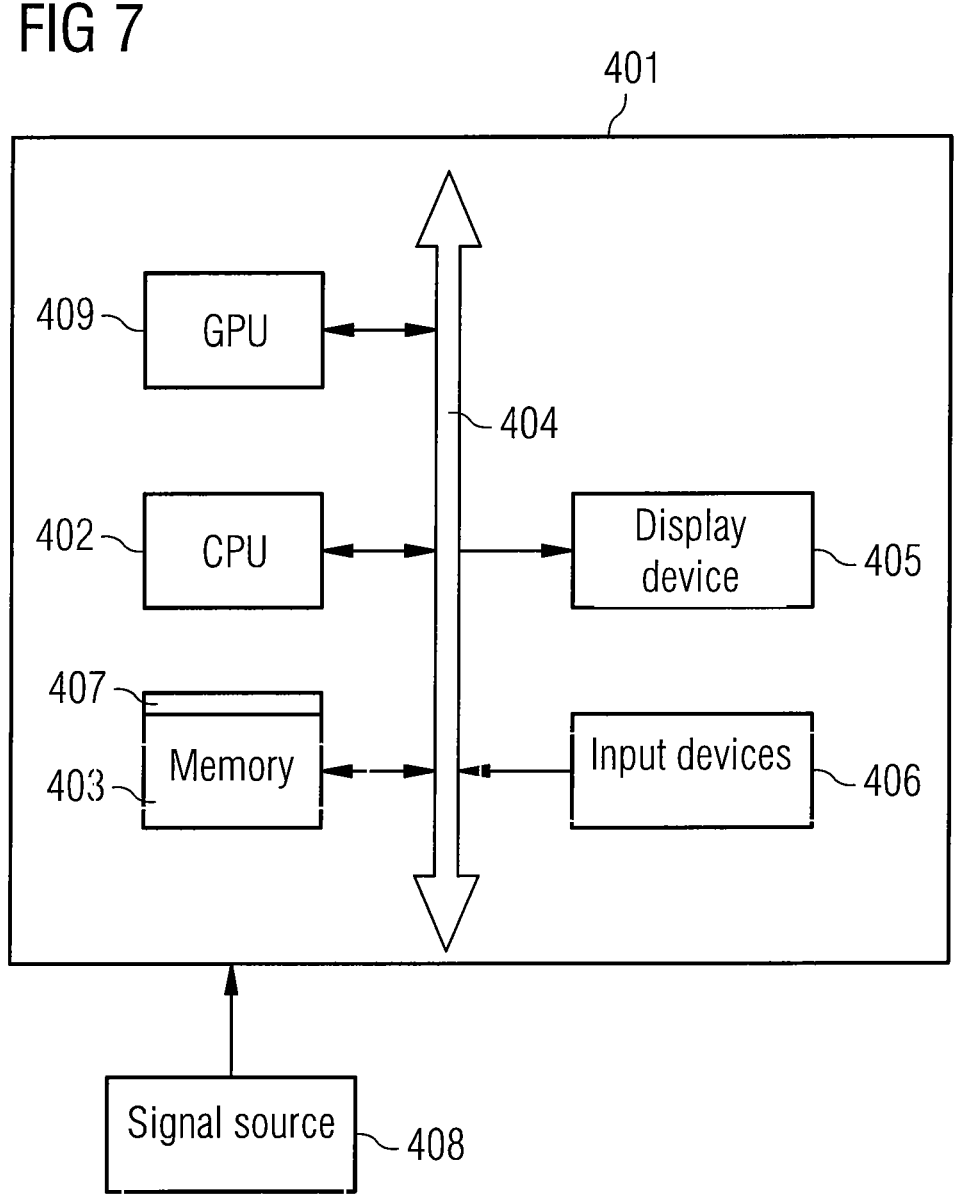
FIG. 7 shows one embodiment of a hardware structure for implementing one embodiment of a method for two-dimensional representation of an object using volume rendering.

With reference to FIG. 7, according to one embodiment, a computer system 401 for GPU-based ray-casting may include, amongst other components, a central processing unit (CPU) 402, a memory 403 and an input/output (I/O) interface 404. The computer system 401 may be coupled via the I/O interface 404 to a display device 405 and various input devices 406 such as a mouse or a keyboard. Auxiliary circuits may include circuits such as a cache, power supply, clock circuits and a communications bus. The memory 403 may include a random access memory (RAM), a read-only memory (ROM), a disk drive, a tape drive, or a combination thereof. The present embodiments may be implemented as a program routine 407 that is stored in the memory 403 and executed by the CPU 402, in order to process the signal from the signal source 408. The computer system 401 also includes a graphics processing unit (GPU) 409 for processing graphics instructions (e.g., for processing the signal source 408 that includes image data). As such, the computer system 401 is a general multipurpose computer system that becomes a special-purpose computer system when the computer system 401 executes the program 407 of the present embodiments.

The computer system 401 also includes an operating system and a micro-instruction code. The various methods and functions described herein may be either part of the micro-instruction code or part of the application program (or a combination thereof), which is executed by the operating system. A variety of other peripheral devices, such as an additional data storage device and a printing device, may be connected to the computer platform.

Since some of the individual system components and method acts, which are presented in the attached figures, may be implemented in software, the actual connections between the system components (or between the process acts) may differ according to the manner in which the present embodiments are programmed.

The present embodiments are not restricted to the applications presented above. The present embodiments may be used for virtual representations in fields other than medical technology. Examples are visualization of products in the area of business and trade and computer games.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for two-dimensional representation of an object using volume rendering, the method comprising:
   providing a representation of the object, in which values of a quantity characterizing the object are given at spatial points of the object;
   calculating, with a processor, with a volume rendering technique, a blended color value for representation as pixels on a screen;
   simulating, only once per blended color value, a single ray emanating from a single external surface of the object for calculating an effect of shadows or an effect of ambient occlusion;
   calculating, only once per blended color value, with the processor, a value for the effect of shadows as a function of the single ray;
   multiplying the blended color value by the value for the effect of shadows in order to obtain a blended color value that takes into account the effect of shadows;
   calculating an additional value for the effect of ambient occlusion; and
   multiplying the additional value by the product of the blended color value and the value for the effect of shadows; or
   multiplying the additional value by a factor that is a measure for light that exists in the ambient area, and adding the multiplied additional value to the product of the blended color value and the value for the effect of shadows; or
   multiplying the product of the additional value and the factor by the blended color value, and adding the multiplied product to the product of the blended color value and the value for the effect of shadows.

2. The method as claimed in claim 1, wherein both the value for the effect of shadows and the additional value for the effect of ambient occlusion are combined with the blended color value in order to obtain a blended color value that takes into account the effect of shadows and the effect of ambient occlusion.

3. The method as claimed in claim 1, wherein the quantity characterizing the object is a density.

4. The method as claimed in claim 1, wherein the surface of the object is an outer surface.

5. The method as claimed in claim 1, wherein the calculated value is filtered before being combined with the blended color value.

6. The method as claimed in claim 1, wherein a length of the single ray is limited.

7. The method as claimed in claim 1, further comprising:
calculating the blended color value for a plurality of pixels;
calculating the value for the effect of shadows for a subset of pixels of the plurality of pixels using a single ray for each pixel of the subset; and
calculating, by interpolation, the value for the effect of shadows for pixels of the plurality of pixels that do not belong to the subset.

8. The method as claimed in claim 1, wherein the calculated value is filtered before being multiplied with the blended color value.

9. A device for two-dimensional representation of an object using volume rendering, the device comprising:
a computer system configured to:
use a representation of the object, in which values of a quantity characterizing the object are given at spatial points of the object;
calculate, with a volume rendering technique, a blended color value for representation as pixels on a screen;
simulate, only once per blended color value, a single ray emanating from a surface of the object for calculating an effect of shadows or an effect of ambient occlusion;
calculate, only once per blended color value, with the single ray, a value for the effect of shadows; and
multiply the blended color value by the value for the effect of shadows in order to obtain a blended color value that takes into account the effect of shadows;
calculate an additional value for the effect of ambient occlusion; and
multiply the additional value by the product of the blended color value and the value for the effect of shadows; or
multiply the additional value by a factor that is a measure for light that exists in the ambient area, and adding the multiplied additional value to the product of the blended color value and the value for the effect of shadows; or
multiply the product of the additional value and the factor by the blended color value, and adding the multiplied product to the product of the blended color value and the value for the effect of shadows; and
a display configured to display an image as a function of the blended color value.

10. The device as claimed in claim 9, wherein the computer system is further configured to combine both the value for the effect of shadows and the additional value for the effect of ambient occlusion with the blended color value in order to obtain a blended color value that takes into account the effect of shadows and ambient occlusion.

11. The device as claimed in claim 9, wherein the quantity characterizing the object is a density.

12. The device as claimed in claim 9, wherein the surface of the object is an outer surface.

13. The device as claimed in claim 9, wherein the computer system is further configured to calculate the value before multiplying the value with the blended color value.

14. The device as claimed in claim 9, wherein a length of the single ray is limited.

15. The device as claimed in claim 9, wherein the computer system is further configured to:
calculate the blended color value for a plurality of pixels;
calculate the value for the effect of shadows for a subset of pixels of the plurality of pixels using a single ray for each pixel of the subset; and
calculate, by interpolation, the value for the effect of shadows for pixels of the plurality of pixels that do not belong to the subset.

16. A non-transitory computer program product for two-dimensional representation of an object using volume rendering by a processor, the computer program product having a computer program that is configured for:
using a representation of the object, in which values of a quantity characterizing the object are given at spatial points of the object;
calculating, with a volume rendering technique, a blended color value for representation as pixels on a screen;
simulating, only once per blended color value, a single ray emanating from a single external surface of the object for calculating an effect of shadows or an effect of ambient occlusion;
calculating, only once per blended color value, using the single ray, a value for the effect of shadows; and
multiplying the blended color value by the value for the effect of shadows in order to obtain a blended color value that takes into account the effect of shadows;
calculating an additional value for the effect of ambient occlusion; and
multiplying the additional value by the product of the blended color value and the value for the effect of shadows; or
multiplying the additional value by a factor that is a measure for light that exists in the ambient area, and adding the multiplied additional value to the product of the blended color value and the value for the effect of shadows; or
multiplying the product of the additional value and the factor by the blended color value, and adding the multiplied product to the product of the blended color value and the value for the effect of shadows.

* * * * *